United States Patent
Bodaghi

(10) Patent No.: US 6,689,242 B2
(45) Date of Patent: Feb. 10, 2004

(54) ACQUISITION/DISTRIBUTION LAYER AND METHOD OF MAKING SAME

(75) Inventor: Hassan Bodaghi, Great Neck, NY (US)

(73) Assignee: First Quality Nonwovens, Inc., State College, PA (US)

(*) Notice: Subject to any disclaimer, the term of this patent is extended or adjusted under 35 U.S.C. 154(b) by 471 days.

(21) Appl. No.: 09/816,666

(22) Filed: Mar. 26, 2001

(65) Prior Publication Data

US 2002/0177378 A1 Nov. 28, 2002

(51) Int. Cl.[7] .............................................. D21H 23/02
(52) U.S. Cl. ...................... 156/181; 156/62.2; 264/122; 264/128; 19/145.7
(58) Field of Search ................................ 156/181, 62.2; 264/122, 128; 19/145.7

(56) References Cited

U.S. PATENT DOCUMENTS

| | | |
|---|---|---|
| 3,607,359 A | 9/1971 | Bischoff et al. |
| 3,616,180 A | 10/1971 | Newman |
| 3,663,348 A | 5/1972 | Liloia et al. |
| 3,772,107 A | 11/1973 | Gentile et al. |
| 3,940,216 A | 2/1976 | Hinckley |
| 4,082,886 A | 4/1978 | Butterworth et al. |
| 4,103,398 A | 8/1978 | Rhyne et al. |
| 4,130,915 A | 12/1978 | Gotchel et al. |
| 4,146,417 A | 3/1979 | Drelich et al. |
| 4,170,680 A | 10/1979 | Cumbers |
| 4,199,400 A | 4/1980 | Bakule et al. |
| 4,300,968 A | 11/1981 | Fottinger et al. |
| 4,336,299 A | 6/1982 | Holst et al. |
| 4,425,126 A | 1/1984 | Butterworth et al. |
| 4,449,978 A | 5/1984 | Iacoviello |
| 4,475,271 A | 10/1984 | Lovgren et al. |
| 4,869,771 A * | 9/1989 | LeVan ........................ 156/289 |
| 4,883,707 A | 11/1989 | Newkirk |
| 4,991,264 A | 2/1991 | Greenway et al. |
| 5,071,681 A | 12/1991 | Manning et al. |
| 5,225,242 A * | 7/1993 | Frankosky et al. ......... 427/209 |
| 5,257,982 A | 11/1993 | Cohen et al. |
| 5,271,780 A | 12/1993 | Baigas, Jr. |
| 5,288,348 A | 2/1994 | Modrak |
| 5,316,601 A | 5/1994 | Hebbard et al. |
| 5,378,528 A | 1/1995 | Makoui |
| 5,399,174 A | 3/1995 | Yeo et al. |
| 5,417,785 A | 5/1995 | Baigas, Jr. |
| 5,418,045 A | 5/1995 | Pike et al. |
| 5,462,793 A | 10/1995 | Isoda et al. |
| 5,486,166 A | 1/1996 | Bishop et al. |
| 5,522,573 A | 6/1996 | Xiao |
| 5,522,810 A | 6/1996 | Allen et al. |
| 5,543,206 A | 8/1996 | Austin et al. |
| 5,543,215 A | 8/1996 | Hansen et al. |
| 5,573,841 A | 11/1996 | Adam et al. |
| 5,587,225 A | 12/1996 | Griesbach et al. |
| 5,589,258 A * | 12/1996 | Maddern et al. ............ 442/382 |
| 5,593,768 A | 1/1997 | Gessner |

(List continued on next page.)

FOREIGN PATENT DOCUMENTS

WO    WO 9518886 A1 * 7/1995 .......... D21H/23/02

*Primary Examiner*—Sam Chuan Yao
(74) *Attorney, Agent, or Firm*—Amster, Rothstein & Ebenstein

(57) ABSTRACT

A nonwoven fabric comprised of a self-sustaining pre-bonded web formed by carding together first relatively thin monocomponent fibers, second relatively thicker monocomponent fibers, and 1–5% bicomponent fibers with the low softening point component thereof bonding together the first, second and bicomponent fibers to form the self-sustaining web. Six to ten percent by weight of cured latex particles are disposed within the fabric and smeared on the outer surfaces of the fabric, the particles being cured in situ to provide enhanced tensile strength to the fabric.

19 Claims, 2 Drawing Sheets

U.S. PATENT DOCUMENTS

| | | | |
|---|---|---|---|
| 5,618,364 A | * 4/1997 | Kwok | ........................ 156/62.8 |
| 5,667,625 A | 9/1997 | Alikhan | |
| 5,674,339 A | 10/1997 | Groeger et al. | |
| 5,707,468 A | 1/1998 | Arnold et al. | |
| 5,710,080 A | 1/1998 | Pellegrini et al. | |
| 5,728,083 A | 3/1998 | Cohen et al. | |
| 5,773,120 A | 6/1998 | Deka et al. | |
| 5,779,847 A | 7/1998 | Groeger | |
| 5,817,394 A | 10/1998 | Alikhan et al. | |
| 5,820,615 A | 10/1998 | Koczab | |
| 5,824,610 A | 10/1998 | Diehl | |
| 5,839,166 A | 11/1998 | Graute | |
| 5,873,964 A | 2/1999 | Kwok | |
| 5,930,871 A | 8/1999 | Raja | |
| 5,968,855 A | 10/1999 | Perdelwitz, Jr. et al. | |
| 6,034,005 A | 3/2000 | Diehl | |
| 6,086,950 A | 7/2000 | Masaki et al. | |
| 6,087,551 A | * 7/2000 | Pereira | ........................ 604/367 |
| 6,150,002 A | 11/2000 | Varona | |
| 6,159,881 A | 12/2000 | Datta et al. | |
| 6,169,045 B1 | 1/2001 | Pike et al. | |

* cited by examiner

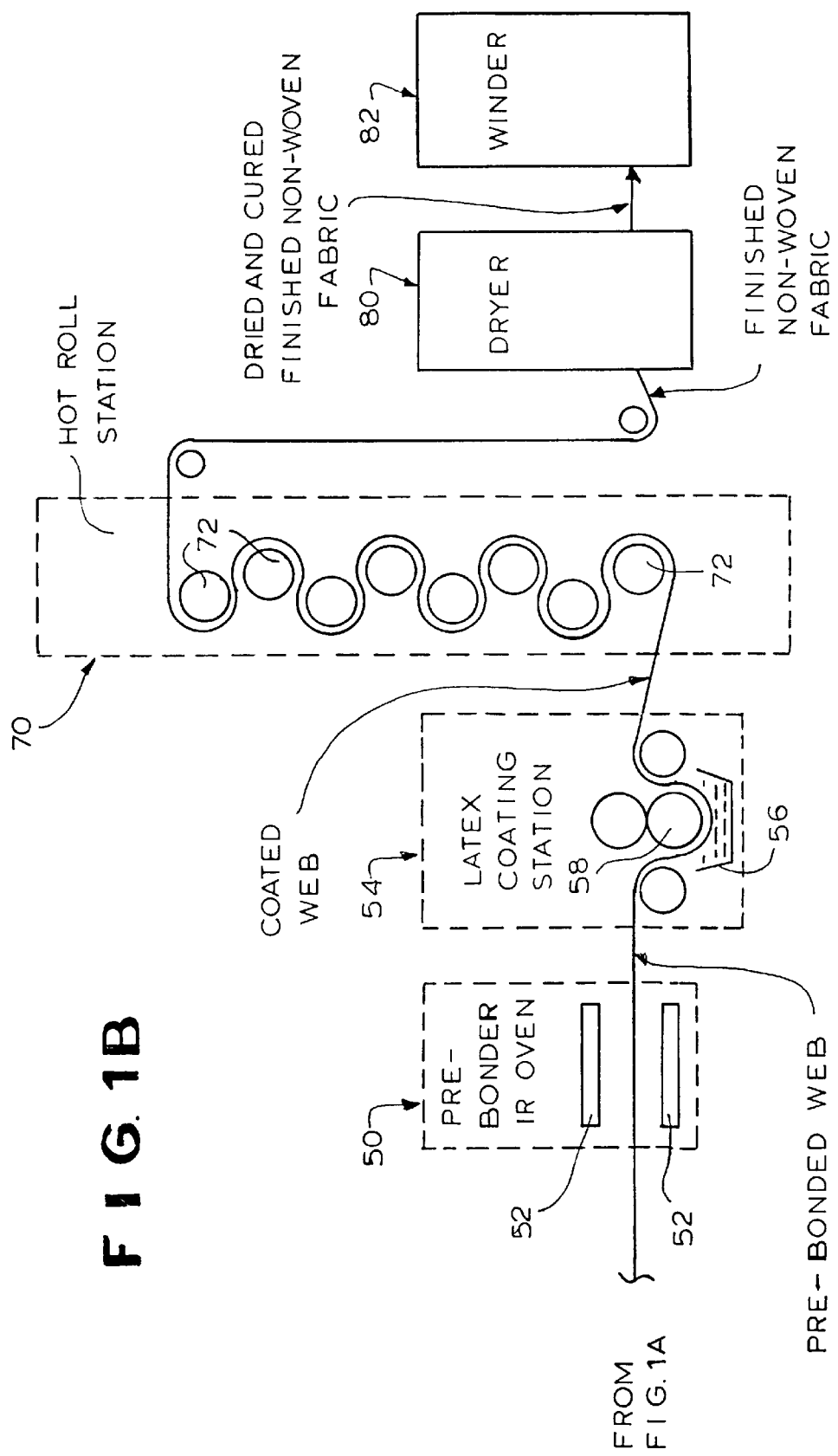

ACQUISITION/DISTRIBUTION LAYER AND METHOD OF MAKING SAME

BACKGROUND OF THE INVENTION

The present invention relates to an acquisition/distribution layer and a method of making the same, and more particularly to such an acquisition/distribution layer which is carded, chemically bonded, and thermally bonded.

Acquisition/distribution (A/D) layers are well known in the diaper art. They should be bulky, soft, and three dimensional to promote bodily fluid distribution over much of the layer's outer surface (adjacent to the cover sheet, which in turn is adjacent to the wearer) before there is substantial absorption of the fluid by the absorbent core located on the other side of the A/D layer. Otherwise the fluid would overwhelm the absorption material at the relatively narrow point of absorption rather than being spread over a wide area of the absorption material surface for superior absorption. Such A/D layers have been made in the past by a variety of different processes as follows:

1. Chemical Bonding. A bale of fibers was opened and carded into a nonwoven web. The nonwoven web was then mixed, at a relatively slow rate of less than 70 meters/minute, with over 25% by weight of a latex binder (including water and expensive latex (rubber) powder), and then the mixture was heated both to chemically cure the latex on the nonwoven and to evaporate the water. This was an expensive, slow and environmentally unfriendly process. The resulting product was stiff and flat as well as expensive due to the high level of latex binder required and the high level of water to be evaporated.

2. Thermal Bonding or "Thermobonding." Bicomponent fibers were incorporated into a carded web at a level of at least 25% and then the carded web was heated to make a thermobonded fabric. While such thermobonded products were bulkier and softer than the chemically bonded nonwovens and could be produced at higher speeds than the chemically bonded materials, the need to use expensive bicomponent fibers increased the cost of such product.

Accordingly, it is an object of the present invention to provide a process which utilizes a newly developed high speed carding process.

Another object is to provide such a process which utilizes a faster and more environmentally friendly chemical bonding process which employs a lower level of latex binder more efficiently and requires less water to be evaporated.

A further object is to provide such a process which utilizes a thermal bonding process which uses a lower level of bicomponent fibers.

It is also an object of the present invention to provide an acquisition/distribution layer which is inexpensive relative to those formed exclusively by chemical bonding or thermal bonding.

It is another object to provide such an A/D layer which is soft, bulky, environmentally friendly, and producible at higher speeds than prior art A/D layers.

SUMMARY OF THE INVENTION

It has now been found that the above and related objects of the present invention are obtained in a method of manufacturing a nonwoven fabric comprising the step of forming a supported carded web. The web includes 75–89% by weight, based on the carded web, of first monocomponent fibers having a first denier of 3 to 7, 10–20% of second monocomponent fibers having a second denier of 8 to 20, the second denier being substantially higher than the first denier, and 1–5% of bicomponent fibers having a denier generally similar to the first denier. The supported carded web is heated to soften one component of the bicomponent fibers. The heated supported carded web is cooled to cause the softened one component to bind together the first, second and bicomponent fibers to form a self-sustaining pre-bonded web. Six–10% by weight latex particles, based on the total fiber of the self-sustaining pre-bonded web, are deposited in the interior and on the exterior of the self-sustaining pre-bonded web—e.g., by passage of the self-sustaining pre-bonded web through a saturation bath. Concurrently, the associated latex particles are smeared over the exterior of the self-sustaining pre-bonded web and the associated latex particles in the interior and on the exterior of the self-sustaining pre-bonded web are cured—e.g., by passage of the self-sustaining pre-bonded web and associated latex particles over heated rolls—to form a bonded web of acceptable tensile strength. Excess moisture is removed from the bonded web to form the nonwoven fabric.

In a preferred embodiment, the first monocomponent fibers are polyester, polyethylene or polypropylene of 3 to 7 denier (preferably 5–6 denier), and the second monocomponent fibers are polyester, polyethylene or polypropylene of 8–20 denier (preferably 10–12 denier). The supported carded web is heated by infrared radiation, preferably to a temperature of at least 170° C. The heated supported carded web is then cooled to a temperature below the softening point of the one component so that the one component of the bicomponent fibers bonds together the first fibers, the second fibers and the other component of the bicomponent fibers. The saturation bath through which the pre-bonded web passes is at a temperature of at least 25° C., and is an emulsion preferably containing at least 8% by weight latex particles. The heated rolls over which the self-sustaining pre-bonded web and associated latex particles are passed over are at least eight steam-heated ceramic rolls at temperatures of from 85° C. up to 190° C. and exert a pressure of about 20 psi on the self-sustaining pre-bonded web. The excess moisture is removed from the bonded web by passage thereof through a hot-air oven at a temperature of at least 200° C. to leave the bonded web with a moisture level of less than 10%. The bonded web has a tensile strength of a least 800 grams/inch in MD and at least 60 grams/inch in CD.

The present invention also encompasses a nonwoven fabric comprising a self-sustaining pre-bonded web formed by carding together 75–89% by weight, based on the total fiber, of first monocomponent fibers having a first denier of 5 to 6, 10–20% of second monocomponent fibers having a second denier of 10 to 12, the second denier being substantially thicker than the first denier, and 1–5% of bicomponent fibers having a denier generally similar to the first denier. The bicomponent fibers have a first component with a low softening point and a second component with a relatively higher softening point, the first component binding together the first, second and bicomponent fibers to form the self-sustaining pre-bonded web. Six to ten percent by weight, based on the total fiber of the self-sustaining pre-bonded web, cured latex particles are disposed within the fabric and smeared on the outer surfaces of the fabric, the particles being cured in situ to provide enhanced tensile strength to the fabric.

In a preferred embodiment, the first and second monocomponent fibers are, independently, polyester, polyethylene or polypropylene, preferably polyester. The first component of the bicomponent fibers bonds together the first fibers, the second fibers and the second component of the bicomponent fibers. The fabric has a moisture level of less than 10% and a tensile strength of at least 800 grams/inch in MD and at least 60 grams/inch in CD.

BRIEF DESCRIPTION OF THE DRAWING

The above and related objects, features and advantages of the present invention which will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1A:
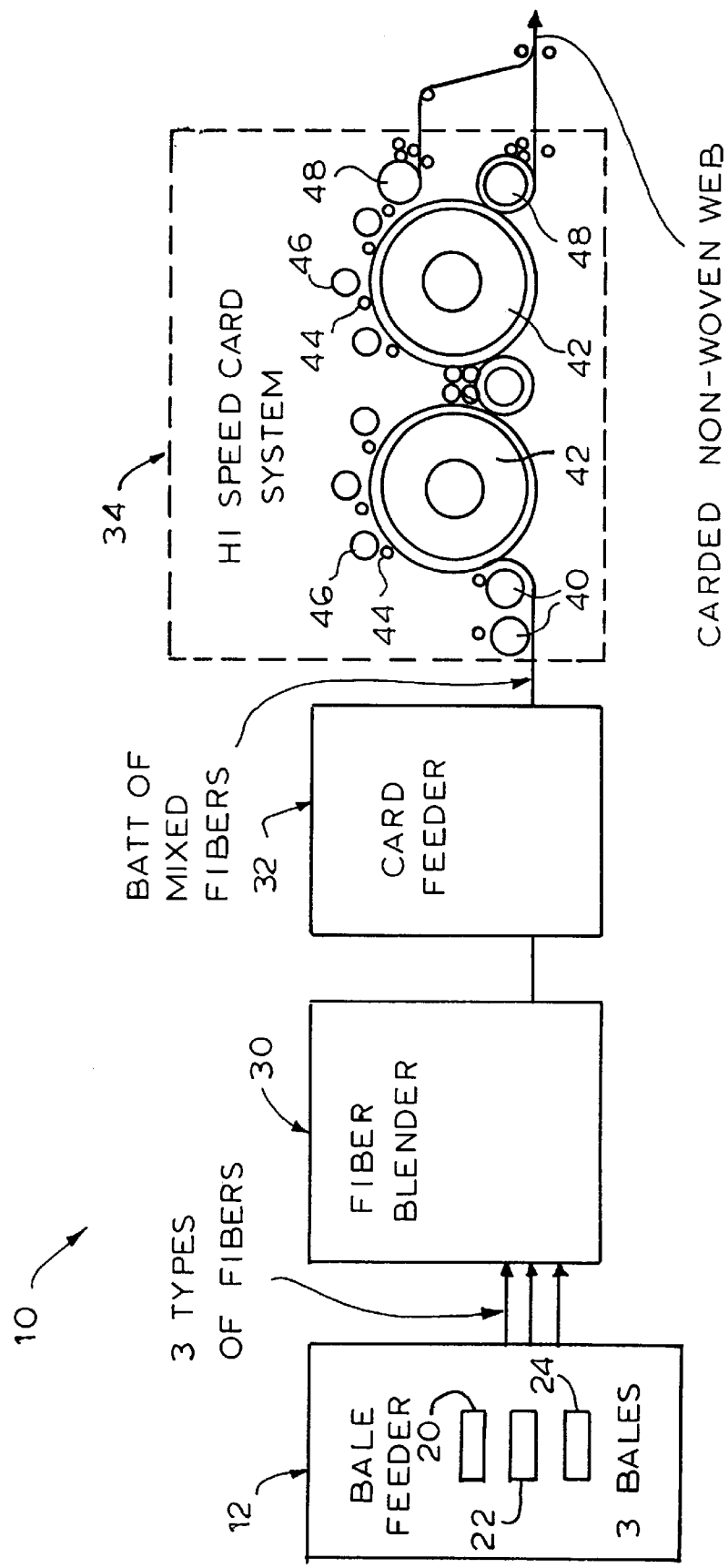
FIG. 1 consists of FIGS. 1A and 1B and is a schematic view of a process for making an acquisition/distribution layer according to the present invention.

Referring now to the drawing, and in particular to FIG. 1 thereof, therein illustrated schematically is apparatus, generally designated by the reference numeral 10, for manufacturing a nonwoven fabric according to the present invention, suitable for use as an acquisition/distribution (A/D) layer—for example, in a diaper or like absorbent product. The A/D layer is bulky, soft and three-dimensional to promote fluid distribution over much of the layer's outer surface before there is substantial absorption of the fluid by the underlying absorbent care.

The apparatus 10 includes a conventional bale feeder, generally designated 12. The bale feeder 12 is designed to accommodate a plurality of bales and to strip the fibers from the bales for transport to a conventional fiber blender, generally designated 30. As illustrated, there are three bales being fed into the bale feeder 12, although a greater number of bales may be used if desired.

One bale consists of first monocomponent fibers 20 having a first denier, one bale consists of second monocomponent fibers 22 having a second denier, and one bale consists of bicomponent fibers 24 having a denier similar to the first denier. The first and second monocomponent fibers 20 and 22 may be of the same or different thermoplastic polymers (such as polyester, polyethylene and polypropylene), polyester being preferred because of its well-known inherently hydrophilic and liquid and vapor absorption/barrier characteristics which make it useful in diaper acquisition/distribution layers.

The bicomponent fibers 24 may have a core/sheath, side-by-side or like structure provided that the two components have substantially different softening temperatures and that, when the structure is a core/sheath, the sheath has the lower softening temperature. Polyester (melting temperature 270° C.), polyethylene (130° C.) and polypropylene (165° C.) are preferred because of their well-known liquid and vapor absorption/barrier characteristics, but, in view of the small amount of bicomponent fibers utilized, the material of which they are constructed is of less concern.

The first denier—that is, the denier of the first monocomponent fibers 20 and the bicomponent fibers 24—is 3 to 8, preferably 5 to 6. Lower denier fibers are more expensive than high denier fibers; further, the high drapability of the low denier fibers may result in a high web density rather than a desirably low web density (which provides the soft, high loft characteristic desired in the final product). Higher denier fibers are cheaper than low denier fibers, but may result in a web of lower softness and lesser drapability so that the density of the final web may be too low to permit effective spreading over the web of an insult (liquid) applied to the web before it becomes absorbed by the absorbent core behind the acquisition/distribution layer. Thus the selection of the appropriate first denier is based on a delicate balance between cost and the ability of the resultant web to function as an acquisition/distribution layer (this in turn depending upon the web density and fiber orientation).

On the other hand, the second denier—that is, the denier of the second monocomponent fibers 22—is substantially thicker than the first denier. The second denier is 8 to 20, preferably 10 to 12. Lower denier fibers may not produce the desired loft or bulk effect, while higher denier fibers may be too bulky and produce a fabric of lower density than required in order to provide the desired distribution of a liquid insult prior to absorption thereof by the absorbent core behind the A/D layer. Thus the selection of the appropriate second denier is also based on a delicate balance having as a primary consideration the bulkiness of the web to be produced, the second denier fibers providing the final product with a desirably high three-dimensional thickness or loft.

Preferably, the bale feeder 12 provides to the fiber blender 30 on a conveyor (not shown) preferably 75–89% by weight of first monocomponent fibers 20, based on the weight on the carded web, 10–20% of second monocomponent fibers 22, and only 1–5% of bicomponent fibers 24. With regard to the preferred range of the second monocomponent fibers 22, lower amounts may fail to provide the necessary bulk for the web, while higher amounts may produce a level of bulkiness which is too great for use as an acquisition/distribution layer, where a thickness of about 4 mm. is typically optimal. Nonetheless, use of the second monocomponent fibers 22 at levels greater than 20% may be useful for particular applications where a bulky web is desirable, for example, filters. With regard to the preferred range of the bicomponent fibers 24, the use of lower levels may not produce a web which will be self-supporting and, while the use of higher levels may produce a web which is even stronger than merely self-sustaining, the bicomponent material fibers 24 are too expensive (relative to the monocomponent fibers 20, 22) for economical use at higher levels. Thus the various fibers 20, 22, 24 are metered by the bale feeder 12 in order to meet production line requirements (such as self-sustaining properties of the web at the time it is fed into the latex coating station), cost limitations and physical properties of the web being produced (the desired web properties being somewhat application dependent). The level of costly bicomponent fibers required for the web is greatly reduced (typically from the prior art level of at least 25% for a "thermo-bonded" web to a preferred 1–5%). The resultant product is accordingly less expensive.

The fiber blender 30 is also conventional in nature and mixes together the three types of fibers being fed to it by the bale feeder 12 to produce a homogeneous fiber mixture for feeding into the card feeder, generally designated 32.

The card feeder 32 is also conventional in nature and merely distributes the fiber mixture received from the fiber blender 14 across the width of the conveyer (not shown) to a uniform thickness in order to form a batt of mixed fibers for delivery into the high-speed card system, generally designated 34.

As illustrated, the high-speed card system 34 is of the type available under the designation HI-SPEED CARD from Spinnbau Corp. of Breman, Germany. Use of a high-speed card system 34 enables the fiber batt to be torn into separate carded fibers at a much higher speed (250–300 meters per minute) than the conventional carding speed (100–150 meters per minute). Accordingly, the production line is able to run at a faster and hence more economical speed.

The card system 34 includes an initial or "breast" section 40 which receives on a conveyor from the card feeder 32 a fiber batt of uniform thickness, preferably 4 to 8 inches thick. The stripper rolls and worker rolls of the breast section 40 pre-open the fibers of the batt while at the same time removing any impurities which may have been accidentally incorporated into the batt (such as metals, plastics and the like). From the breast section 40 the batt passes over two main carding rolls 42 having wires disposed thereon to open the fibers in the batt. Disposed above the main rolls 42 are stripper rolls 44 which grab the unopened fibers or neps of the batt and pass them to worker rolls 46 which return the unopened fibers for a second pass over the main rolls 42. After passage over the two main rolls 42, the now fully opened and separated fibers of the batt are received by a pair of doffers 48. The doffers 48 are take-off rolls which rotate at a lower speed than the main rolls 42 for removal of the carded non-woven web from the card system 34 and passage thereof into a pre-bonder, generally designated 50. Typically "scramble rolls" 49 are associated with one or both of the doffers 48 both to randomize the fiber orientation and create an isotropic distribution and to provide controlled loft or three-dimensionality to the web leaving the doffers 48.

Carding is a well-known operation in the non-woven art, and the individual elements of a card system are well-known to those skilled in the art. Accordingly, it is not deemed necessary to provide further details thereof herein.

The carded nonwoven web is then transported by a conveyer from the card system 34 through the pre-bonder 50, which preferably consists of an infrared (IR) oven. The IR oven 50 need be nothing more complex than two banks of IR heating units 52, one disposed above the travel path of the carded non-woven web and one disposed below the travel path of the carded non-woven web and the IR-transparent conveyer transporting the web through the pre-bonder 50. Passage of the web through the pre-bonder 50 is effective to raise the temperature of the web to a temperature sufficient to cause softening of the lower softening point component of the bicomponent fibers 24, at least 170° C. (preferably 180° C.–210° C.).

Heating of the supported carded web to a temperature where one component of the bicomponent fibers 24 softens, is followed by ambient cooling of the heated supported carded web to a temperature where the softened one component re-solidifies and binds together the first, second and bicomponent fibers 20, 22 24 to form a pre-bonded web. The pre-bonded web is self-sustaining and no longer requires the support of a conveyer.

After cooling, the self-sustaining pre-bonded web is passed into a latex coating station, generally designated 54. The latex coating station 54 applies an emulsion of latex particles to the web by passing the web through a saturation bath 56, preferably a bath containing a padder 58. Preferably the saturation bath 56 is at a temperature of at least 25° C. and contains at least 8% by weight of latex particles. The padder 58 is a rubber roll having internal pistons which reciprocate to ensure complete saturation of the web by the bath through which it is being passed. The padder permits application of the latex binder at a very high speed without messy splashing, enables a reduction of the latex binder/ fiber mix ratio, and increases the processing speed to over 200 meters per minute (relative to the prior art chemical bonding machines operating at less than 70 meters per minute). It is important that the latex particles are applied not only to both external major surfaces of the web (i.e., the top and bottom surfaces), but also, to the extent possible, into the interior of the web. It will be appreciated that the passage of the web through the pre-bonder 50 is an essential step in the production line as it enables the web to become self-sustaining so that the coating station 54 can apply the latex particles most optimally via a saturation bath.

The coating station 54 includes after the bath at least a pair of conventional squeeze rolls (not shown) which remove excess amounts of the bath (the bath liquid and the latex particles) from the web. Typically the amount of bath removed from the web is adjustable to produce a desired dry pick-up level. The squeeze rolls are set to insure that the dry pick-up of latex particles by the web is not greater than 10%, preferably 6-10%. The percentage latex particles in the saturation bath may differ from the ultimately desired dry pick-up (for example, 5–50% latex particles in the bath) but, if low, the squeeze rolls must squeeze out a greater amount of water from the wet pick-up and, if high, expensive latex particles may be wasted.

The dry pick-up level of the latex particles by the web is greatly reduced from that used in the prior art process relying purely on chemical binding (10% or less versus at least 25% in the prior art). This results in a more economical product as well as one which is more environmentally friendly due to the lower use of latex.

Next, the self-sustaining pre-bonded web and associated latex particles from the coating station 54 are transferred to a hot roll station, generally designated 70. The hot roll station 70 contains a series or stack of heated rolls 72 which concurrently (a) gradually evaporate the moisture from the latex, (b) smear or flatten the associated latex particles (on the exterior web surfaces) over the exterior of the web and into the web interior, and (c) cure the associated latex particles (both in the interior and on the exterior of the web) to form a bonded web of acceptable tensile strength. From 5 to 16, but preferably 8, rolls 72 are used. As is customary in the art, compensators (not shown) are disposed along the production line, and in particular before and after the hot roll station 70, so as to create and regulate the tension in the web as it passes over the rolls 72 therein. The compensators cause the web to exert about 20 psi pressure on the rolls 72. The rolls 72 are heated, preferably by superheated pressurized (200 psi) steam to successively higher temperatures. Preferably the first roll is at 85° C. and the last roll is at 190° C.

The concurrent (simultaneous) smearing and curing of the latex particles by the hot rolls 72 is critical to the development of ultimate web strength because otherwise the uncured smeared latex particles will rebound to their original configuration prior to curing.

The rolls 72 are preferably ceramic-coated, although alternatively TEFLON-coated or silicon-coated rolls may be used. The surface of rolls must be smooth enough to spread (smear) the associated latex particles over the exterior surfaces of the web and preferably force or squeeze some of the latex particles from the surfaces into the interior of the web. Preferably the rolls are of a lightweight, metallic material suitable for the temperatures involved and possessing a high modulus of elasticity, while the coating preferably has a low surface tension.

The smearing of the associated latex particles on the exterior surfaces of the web by the rolls 72, as well as the forcing of additional latex particles from the exterior surfaces of the web into the interior thereof, enables the web to achieve a tensile strength better or at least comparable to the prior art webs, although only a small fraction (preferably less than 50%) of the quantity of latex particles used in the prior art are on the web. The smearing or spreading of the latex particles enhances the ability of the latex, upon cure, to act as a binder or adhesive and thereby increases the tensile strength of the web.

The web emerging from the hot roll station 70 is basically a finished non-woven fabric and is passed into a dryer, generally designated 80, to remove any excess moisture. The dryer also completes curing of the latex particles by curing any particles not cured in the hot roll station 70. Typically almost all of the latex particles associated with the web are cured in the hot roll station 70, with only a relatively minute number of the associated latex particles requiring further final curing in the dryer 80. Preferably the dryer 80 is a hot air oven having a temperature of at least 200° C. to remove the excess moisture and leave the bonded web with a moisture level of less than 10% and substantially all latex particles associated with the web cured. The oven of the dryer is optimally a hot air through oven so that the passage of heated air through the web contributes to the desired bulkiness and loft thereof.

The dried and cured finished non-woven fabric is then passed from the dryer 80 into a conventional winder, generally designated 82, for take-up and storage.

The final web product has a tensile strength of at least 800 grams per inch MD and at least 60 grams per inch CD.

It will be appreciated that the reduction in the amount of latex binder used is made possible basically because the "pre-bonded" web has sufficient integrity to be passed through a "saturation" bath which saturates the web with the latex binder. This is preferable to the prior art chemical bonding techniques of merely spraying one or both web surfaces with the latex binder or applying the latex binder as a foam to one or both web surfaces, as neither of these prior art techniques is effective in driving the latex binder into the interior of a bulky web material. By way of contrast, the passage of the web through a bath saturates the entire thickness of the web more uniformly, especially where the web is relative thick. Additionally, the use of a conventional padder in the bath assists in relocating at least some of the latex binder initially resting on the exterior surfaces of the web into the interior of the web.

A further factor enabling the use of a lesser amount of latex binder than in the prior art is the passage of the web (after the bath) through a series of steam-heated ceramic rollers. These rollers spread the latex binder on the surfaces of the web so as to more evenly distribute the latex binder on the surfaces (than if it remained as latex particles) and thus ensure that the cured latex binder provides the web with the desired level of tensile strength.

The use of the lower latex binder levels in turn makes the product of the present invention softer and cheaper than a purely chemically bonded web, while the use of some latex binder makes the product stronger than a purely thermo-bonded web (which lacks any latex binder). The final product is produced at rates as much as three times higher than the product of a purely chemically bonded system, and much more cheaply than the product of a thermobonding system requiring a large amount of relatively expensive bicomponent fibers.

The interrelatedness of the various features of the present invention should be appreciated. Thus, the use of bicomponent fibers and the pre-bonding station provides the pre-bonded web with its self-sustaining character (that is, the low melting point component of the bicomponent fiber softens and, upon cooling, causes the development of sufficient strength and integrity in the web to allow it to be passed through the coating station saturation bath). The use of thick second denier fibers provides the desirable three-dimensional thickness or loft in the final product (despite the reduction in the percentage of bicomponent fibers used). The use of a chemical binder (i.e., the latex binder) provides strength to the web, and the use of the hot steam ceramic roller station not only more efficiently utilizes the smaller amount of latex binder by concurrently smearing and curing the latex binder that is present on the outer surfaces of the web, but also develops the final strength of the web before it passes through the dryer (so that the dryer is basically necessary only for the final removal of moisture, and not for the development of strength in the web).

The final product provides a superior acquisition/distribution layer relative to the prior art as the product is not as stiff and flat as in a purely chemically bonded layer and is as bulky and soft as a "thermo-bonded" layer, while affording the advantages of lower material costs (due to lower levels of bicomponent fibers and latex binder) and lower production costs (due to the higher speeds at which the production line may be operated).

While bicomponent fibers have been described as the preferred mechanism for achieving pre-bonding of the mixed fibers in the pre-bonder 50, in view of the high costs of bicomponent fibers relative to monocomponent fibers, it may be desirable to use in place of the bicomponent fiber a monocomponent fiber having a lower softening temperature than the first and second monocomponent fibers. For example, a monocomponent polyethylene fiber may be substituted for a polypropylene/polyethylene bicomponent fiber.

While a saturation bath has been illustrated as the preferred latex coating apparatus in station 54, clearly other conventional means for applying a coating of latex particles on a web may be employed—for example, a double kiss roll applicator—or the latex particles may be applied as a foam or paste by other means well known in the art, provided that the web interior is substantially saturated by the latex particles.

The following example illustrates the efficacy of the present invention.

EXAMPLE

An acquisition/distribution layer was made by blending three different poly(ethylene terephthalate) fibers as follows: 80% monocomponent PET of 7.4 denier, 15% monocomponent PET of 13.2 denier, and 5% bicomponent PET of 5.3 denier. The fibers were blended and then fed through a laboratory version of the high-speed card system (running at 25 meters per minute). Two scramble rolls were disposed on each duffer to randomize the fiber orientations and trade an isotropic fiber orientation distribution in the web. The web was fed through a pre-bonder IR oven at 170° C. The pre-bonded web was then fed through a saturation bath equipped with a padder. The bath contained latex binder (available from BSAF under the trade name STYROFAN 830) with foaming and wetting agents, stabilizers, and pH control agents to maintain the bath at a pH of 6–8. The dry pick-up was 5% latex. The fully saturated web and associated latex particles were then fed through a stack of eight superheated ceramic-coated rolls (the first roll surface temperature being 85° C. and successive roll surface temperatures being increased by 15° C. up to the last roll at 190° C.). The web was under a tension of 20 psi. The finished nonwoven fabric was then sent through a hot air oven set at 200° C. to complete drying and finishing, and then collected on an automatic winder.

The resultant fabric had a tensile strength in the machine direction (MD) of 17 N (Newtons) and in the cross direction (CD) of 14 N, the elongation at break being about 20% in both directions.

Specimens of the fabric thus produced were tested for both acquisition speed (in seconds) after first, second and third insults, and for re-wet or dryness (in grams) after first, second and third insults. One specimen was tested using as the absorbent core NOVATHIN (250 gsm) available from Rayonier, and the other was tested using medium protective underwear available from First Quality Products, Inc. The specimens had a basis weight of 40 gsm, a thickness of 2.8 mm and a density of 0.030 g/cc. The test results are set forth in the TABLE.

To summarize, the present invention provides a process which utilizes a newly developed high speed carding process, a faster and more environmentally friendly chemical bonding process (which employs a lower level of latex binding more efficiently), and a faster and more economical thermo-bonding process (which employs a lower level of bicomponent fibers) in order to produce an acquisition/distribution layer which is inexpensive relative to those formed exclusively by chemical bonding or thermal bonding. The acquisition/distribution layer is soft, bulky, environmentally friendly and producible at higher speeds than a prior art acquisition/distribution layer.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

TABLE

| Rayonier NOVATHIN 250 gsm | | |
| --- | --- | --- |
| Acquisition Speed (sec) | Insult #1 | 13 |
| | 2 | 15 |
| | 3 | 20 |
| Re-wet/Dryness (g) | Insult #1 | 0.25 |
| | 2 | 10.6 |
| | 3 | 14 |
| Medium protective underwear | | |
| Acquistion Speed (sec) | Insult #1 | 12 |
| | 2 | 13 |
| | 3 | 14 |
| Re-wet/Dryness (g) | Insult #1 | 0.17 |
| | 2 | 2.6 |
| | 3 | 8.2 |

I claim:

1. A method of manufacturing a nonwoven fabric comprising the steps of:
   (A) forming a supported carded web including:
      (i) 75–89% by weight, based on the carded web, first monocomponent fibers having a first denier of 3 to 7,
      (ii) 10–20% second monocomponent fibers having a second denier of 8 to 20, the second denier being substantially higher than the first denier, and
      (iii) 1–5% bicomponent fibers having a denier generally similar to the first denier;
   (B) heating the supported carded web to a temperature where one component of the bicomponent fibers softens;
   (C) cooling the heated supported carded web to a temperature where the softened one component binds together the first, second and bicomponent fibers to form a self-sustaining pre-bonded web;
   (D) depositing 6–10% by weight latex particles, based on the total fiber of the self-sustaining pre-bonded web, throughout the interior and on the exterior of the self-sustaining pre-bonded web;
   (E) concurrently smearing and curing the associated latex particles in the interior and on the exterior of the self-sustaining pre-bonded web to form a bonded web of acceptable tensile strength, and
   (F) removing excess moisture from the bonded web to form the nonwoven fabric.

2. The method of claim 1 wherein the first and second monocomponent fibers are independently polyester, polyethylene or polypropylene.

3. The method of claim 2 wherein the first and second monocomponent fibers are polyester.

4. The method of claim 1 wherein the supported carded web is heated by infrared radiation.

5. The method of claim 1 wherein the supported carded web is heated to a temperature of at least 17° C.

6. The method of claim 1 wherein the heated supported carded web is cooled to a temperature below the softening point of the one component.

7. The method of claim 1 wherein the one component of the bicomponent fibers bands together the first fibers, the second fibers and the other component of the bicomponent fibers.

8. The method of claim 1 wherein the latex particles are deposited in throughout the interior and on the exterior of the web by passing the self-sustaining pre-bonded web through a saturation bath.

9. The method of claim 8 wherein the saturation bath is at a temperature of at least 25° C., and is an emulsion containing at least 8% by weight latex particles.

10. The method of claim 1 wherein the self-sustaining pre-bonded web and associated latex particles are passed over a series of heated rolls to concurrently smear and cure the associated latex particles.

11. The method of claim 10 wherein the heated rolls are steam-heated ceramic rolls.

12. The method of claim 10 wherein the series of heated rolls begin at a temperature of about 85° C. and end at a temperature of about 190° C., and the self-sustaining pre-bonded web exerts a pressure of about 20 psi thereon.

13. The method of claim 10 wherein the self-sustaining pre-bonded web and associated latex particles are passed over a series of at least 8 of the heated rolls.

14. The method of claim 1 wherein the bonded web has a tensile strength of at least 800 grams/inch in MD and at least 60 grams/inch in CD.

15. The method of claim 1 wherein the excess moisture is removed from the bonded web by passage thereof through a hot-air oven at a temperature of at least 200° C. to leave the bonded web with a moisture level of less than 10%.

16. The method of claim 1 wherein the first denier is about 5–6, and the second denier is about 10–12.

17. A method of manufacturing a nonwoven fabric comprising the steps of:
   (a) forming a supported carded web including:
      (i) 75–89% by weight, based on the carded web, first fibers having a first denier of 3 to 7 and a first softening temperature,
      (ii) 10–20% second fibers having a second denier of 8 to 20 and a second softening temperature, the second denier being substantially higher than the first denier, and (iii) 1–5% third fibers having a denier generally similar to the first denier and a softening temperature lower than the first and second softening temperatures;

(B) heating the supported carded web to a temperature where the third fibers soften;

(C) cooling the heated supported carded web to a temperature where the third fibers bind together the first, second and the third fibers to form a self-sustaining pre-bonded web;

(D) depositing 6–10% by weight latex particles, based on the total fiber of the self-sustaining pre-bonded web, in the interior and on the exterior of the self-sustaining pre-bonded web by passing the self-sustaining pre-bonded web through a saturation bath;

(E) concurrently smearing the associated latex particles over the exterior of the self-sustaining pre-bonded web and curing the associated latex particles in the interior and on the exterior of the self-sustaining pre-bonded web to form a bonded web of acceptable tensile strength; and (F) removing excess moisture from the bonded web to form the nonwoven fabric.

18. The method of claim 17 wherein the latex particles are deposited throughout the interior and on the exterior of the web.

19. The method of claim 17 where the self-sustaining pre-bonded web and associated latex particles are passed over a series of heated rolls to concurrently smear and cure the associated latex particles.

* * * * *